United States Patent
Shalaby

(10) Patent No.: US 7,694,815 B2
(45) Date of Patent: Apr. 13, 2010

(54) PACKAGE COMPONENTS FOR RADIOCHEMICAL STERILIZATION

(75) Inventor: Shalaby W Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 127 days.

(21) Appl. No.: 12/157,516

(22) Filed: Jun. 11, 2008

(65) Prior Publication Data

US 2008/0286144 A1 Nov. 20, 2008

Related U.S. Application Data

(63) Continuation-in-part of application No. 11/228,719, filed on Sep. 16, 2005.

(60) Provisional application No. 60/610,658, filed on Sep. 17, 2004.

(51) Int. Cl.
*A61L 2/08* (2006.01)

(52) U.S. Cl. ............... 206/438; 206/439; 206/528; 422/22; 422/28; 422/292; 250/455.11

(58) Field of Classification Search ............... 422/22, 422/28, 32, 292, 294; 250/455.11; 206/438, 206/439, 528
See application file for complete search history.

(56) References Cited

U.S. PATENT DOCUMENTS

| 5,422,068 A | 6/1995 | Shalaby et al. |
| 2003/0069535 A1* | 4/2003 | Shalaby ............ 604/48 |
| 2007/0065334 A1 | 3/2007 | Shalaby |

* cited by examiner

*Primary Examiner*—Sean E Conley
(74) *Attorney, Agent, or Firm*—Leigh P Gregory

(57) ABSTRACT

Package components for the radiochemical sterilization of medical devices contain paraformaldehyde as the precursor of the radiolytically generated, sterilizing dose of formaldehyde, premixed with a particulate solid dispersant of, preferably, polyethylene or silica gel, which facilitates the free passage of the formaldehyde to the package gaseous environment or additionally, absorbs trace amounts of moisture in the package, thus, facilitating the device manufacturing process and increasing shelf-stability.

20 Claims, No Drawings

PACKAGE COMPONENTS FOR RADIOCHEMICAL STERILIZATION

This application is a continuation-in-part of U.S. Ser. No. 11/228,719, filed on Sep. 16, 2005, which claims the benefit of prior provisional U.S. Ser. No. 60/610,658, filed on Sep. 17, 2004.

FIELD OF THE INVENTION

The present invention is directed to two sets of specialty tailored package components for use in the radiochemical (RCS) process of medical devices in hermetically sealed foil packs using a combination of low-dose, high-energy radiation and paraformaldehyde, as a highly effective source of radiolytically generated formaldehyde gas, in combination with an inert or adsorbing solid dispersant wherein either of said combinations are contained in a porous barrier adjacent to a perforated device holder, or a liquid formulation in a sealed, flexible dispenser.

BACKGROUND OF THE INVENTION

Prior application U.S. patent application Ser. No. 11/228,719, filed on Sep. 16, 2005, by one of the present inventors has dealt with package components for radiochemical sterilization of medical or pharmaceutical products consisting of a hermetically sealed foil pack containing (1) a solid device, as in absorbable sutures and meshes, in a perforated holder or a liquid formulation in a sealed, flexible dispenser, as in absorbable cyanoacrylate-based tissue adhesive; (2) a microparticulate, unstabilized polyformaldehyde as a source of radiolytically generated formaldehyde encased in a sealed pouch comprising a porous, non-woven or woven fabric; and (3) a nitrogenous compound capable of reacting with residual formaldehyde, such as melamine or urea, that is encased in a sealed pouch comprising a porous, non-woven or woven fabric. However, only a small fraction representing less than 3 weight percent of the microparticles of unstabilized polyformaldehyde used to produce formaldehyde gas radiolytically was responsible for releasing the sterilizing dose of the formaldehyde gas. This leaves more than 95 percent of unused polymer mass. Such behavior may be attributed to the establishment of equilibrium between the monomeric and polymeric formaldehyde, which compromises the efficiency of the formaldehyde precursor. This provided an incentive to pursue the study associated with the instant invention, which entails the use of (1) a cyclic, thermodynamically less stable formaldehyde precursor compared to the linear polymeric polyformaldehyde described in the parent application; (2) an organic polymeric microparticular dispersant that lowers the mass of the active gas precursor per unit volume in the package insert, which facilitates the gas diffusion and minimizes the overall mass of the precursor; and (3) an organic granular desiccant dispersant, which not only lowers the mass of the precursor, but also acts as a desiccant to maximize the shelf-life stability of the sterilized absorbable device.

SUMMARY OF THE INVENTION

In a general aspect of the present invention is directed to a hermetically sealed package for use in radiochemical sterilization of at least one medical device contained therein which includes an essentially gas impervious, moisture impervious sealed outer sheet, a holder for the medical device, and a sealed, porous pouch contained within the sealed outer sheet and containing a mixture of radiolabile paraformaldehyde particles and radiostable dispersant powder at a weight ratio of less than 1:2, wherein the outer sheet comprises a laminated foil and the porous pouch comprises a non-woven fabric construct of a polyolefinic material selected from polyethylene, polypropylene, and ethylene-propylene copolymer.

A specific aspect of this invention deals with a hermetically sealed package for use in radiochemical sterilization of at least one medical device contained therein which includes an essentially gas impervious, moisture impervious sealed outer sheet, a holder for the medical device, and a sealed, porous pouch contained within the sealed outer sheet and containing a mixture of radiolabile paraformaldehyde particles and radiostable dispersant powder at a weight ratio of less than 1:2, wherein dispersant powder is an organic polymer selected from polyethylene, polypropylene, polyethylene terephthalate, and polytetramethylene terephthalate. Alternatively, the dispersant powder is an inorganic desiccant, such as silica gel.

A special aspect of the invention deals with a hermetically sealed package for use in radiochemical sterilization of at least one medical device contained therein which includes an essentially gas impervious, moisture impervious sealed outer sheet, a holder for the medical device, and a sealed, porous pouch contained within the sealed outer sheet and containing a mixture of radiolabile paraformaldehyde particles and radiostable dispersant powder at a weight ratio of less than 1:2, wherein the holder is a perforated folder made at least one material selected from cellulose, polyethylene, polypropylene, ethylene-propylene copolymer, and polyethylene terephthalate, and wherein the medical device can be (a) an absorbable suture, (b) an absorbable composite surgical mesh, (c) a partially absorbable composite surgical mesh, (d) a partially absorbable composite vascular repair device, (e) a composite urinary bladder repair device, (f) a composite polymeric stent for repairing at least one body conduit selected from ureters, urethra, blood vessels, and esophagi, or (g) an absorbable composite device for internal bone fixation.

A second special aspect of this invention deals with a hermetically sealed package for use in radiochemical sterilization of at least one medical device contained therein which includes an essentially gas impervious, moisture impervious sealed outer sheet, a holder for the medical device, and a sealed, porous pouch contained within the sealed outer sheet and containing a mixture of radiolabile paraformaldehyde particles and radiostable dispersant powder at a weight ratio of less than 1:2, wherein the medical device is a cyanoacrylate tissue adhesive and the holder therefor is a gas-tight container, wherein the gas-tight container is a sealed, squeezable ampoule formed from a polymer selected from polyethylene, polypropylene, ethylene-propylene copolymer, and polyethylene terephthalate. Alternatively, the gas-tight container is a screw-capped glass vial.

A third special aspect of the invention deals with a hermetically sealed package for use in radiochemical sterilization of at least one medical device contained therein which includes an essentially gas impervious, moisture impervious sealed outer sheet, a holder for the medical device, and a sealed, porous pouch contained within the sealed outer sheet and containing a mixture of radiolabile paraformaldehyde particles and radiostable dispersant powder at a weight ratio of less than 1:2, wherein the medical device is a self-setting, composite absorbable bone cement or bone filler and the holder therefor is a squeezable, gas-tight container, and wherein the bone cement or bone filler preferably is a cyanoacrylate monomer.

A technologically important aspect of this invention deals with a hermetically sealed package for use in radiochemical sterilization of at least one medical device contained therein which includes an essentially gas impervious, moisture impervious sealed outer sheet, a holder for the medical device, and a sealed, porous pouch contained within the sealed outer sheet and containing a mixture of radiolabile paraformaldehyde particles and radiostable dispersant powder at a weight ratio of less than 1:2, wherein the hermetically sealed package is radiochemically sterilized by irradiating the package with gamma rays or E-beam at a dose of less than 11 kGy.

DETAILED DESCRIPTION OF PREFERRED EMBODIMENTS

This invention presents substantial improvements over the prior art on radiochemical sterilization, which, in turn, makes this technology more practical to use and adds new packaging attributes pertaining to the ease of package assembling and shelf-stability of radiochemically sterilized, absorbable medical devices. From a technological perspective this invention teaches the use of smaller amounts of paraformaldehyde, comprising a low melting mixture ($T_m$<150° C.) and low molecular weight oxymethylene-based chains, as a more effective source of formaldehyde compared to the linear, high molecular weight, high melting ($T_m$>160° C.) polyformaldehyde known as Celcon® from Celanese, which is relatively less responsive to radiolysis under the typical radiochemical sterilization dose (3 to 11 kGy), less than 3 weight percent depolymerized to formaldehyde, and the unused polymer remains in the pouch as an unnecessary component. From a second technological perspective, the present invention provides a preferred alternative to the use of practically pure polyformaldehyde microparticles as the source of formaldehyde, which interferes with the fugacity (or tendency to escape) of the radiolytically formed formaldehyde into the gas phase surrounding the medical device. As the formed formaldehyde migrates through the intact mass of polyformaldehyde, part of it repolymerizes on the surface of the polyformaldehyde particles, thus establishing a monomer-polymer equilibrium that compromises the effectiveness of the radiolytic process. To address this inefficiency, the present invention teaches the use of solid, chemically-unrelated-to formaldehyde particulate dispersant as a thoroughly mixed combination of at least 2:1 weight ratio with a low molecular weight thermodynamically less stable source of formaldehyde, which facilitates the free passages and increases the sterilizing efficiency of the radiolytically formed gas since it (1) does not represent a reactive surface at which the formaldehyde gas can establish a monomer-polymer equilibrium; (2) reduces the required mass of the formaldehyde precursor to produce the sterilizing dose of the gas; and (3) leaves mostly an inert material in the irradiated package—typical dispersants comprise polyethylene, ethylene-propylene copolymer, polypropylene, and polyethylene terephthalate. The polyethylene particles may comprise low density, high density, linear-low density, and/or ultrahigh molecular weight polyethylene (UHMW-PE). From a packaging perspective, the present invention provides two basic advantages over the prior art. First, using a combination of the formaldehyde-precursor and a practically formaldehyde-irrelevant dispersant facilitates the assembling of the porous pouch containing said precursor and insures safe handling by the assembling personnel. Second, the use of desiccant dispersants introduces a unique feature to the packaging technology of medical devices comprising absorbable polymers which undergo detrimental degradation in hermetically sealed packages containing trace amounts of moisture—typical desiccant dispersants include silica gel. In effect, the desiccant dispersant, such as silica gel, not only facilitates the free passage (or diffusion) of the formaldehyde to gas phase of the package, but also absorbs traces of moisture that may have been present, inadvertently, in the package prior to irradiation. Trapping traces of moisture (1) improves the post-irradiation shelf-life of the absorbable solid device; and (2) eliminates or minimizes the radiation-induced conversion of water molecules into hydroxyl radicals in the package, which can lead to additional radiation-oxidation degradation of the absorbable medical device during irradiation, as part of the so called secondary radiation degradation events during or following the irradiation. Third, in packages containing cyanoacrylate-based tissue adhesive, removal of water by the desiccant dispersant eliminates the risk of slow diffusion of water through the walls of the polymeric container housing the cyanoacrylate tissue adhesive, which will undergo premature water-activated polymerization—the use of a desiccant dispersant, such as silica gel, indirectly increases the cyanoacrylate shelf-life.

Further illustrations of the present invention are provided by the following examples:

Example 1

Radiochemical Sterilization (RCS) of Suture Braids Using Different Combinations of Paraformaldehyde and Ultrahigh Molecular Weight Polyethylene (UHMW-PE)

A number of vacuum dried 27 inch lengths of size 2-0 braided sutures were individually placed in a predried, perforated paper folder and placed in groups of 3"×5" laminated foil packs having a sealed, non-woven polyethylene (Tyvek®) porous pouch filled with different combinations of paraformaldehyde and UHMW-PE (PF-UPE) with an average particle size of >20 micron and <200 micron, respectively, in the presence or absence of a spore strip as an internal control. Descriptions of the different packs are given in Table I. The unsealed foil packs containing the different PF-UPE combinations with and without the spore strip were prepurged twice with dry nitrogen and hermetically sealed. The sealed packs were gamma irradiated with about 5 kGy using a Co-60 source at a dose rate of 32 kGy/hr. The irradiated packs were divided into separate groups and tested at two weeks following irradiation using standard techniques needed to determine (1) the residual formaldehyde in the package; and (2) reduction in spore count of the spore strip. The compositions of the different pouches used in the RCS study of Example 1 are described in Table I. The preparation of the specific groups of pouches is outlined below.

The paraformaldehyde (PF) was purchased from Aldrich in powder form. An UHMW-PE (UPE) was also used a powder with an average particle size of <200 μm. The PF and UPE powders were mixed in three different mass ratios to produce three sets of samples. The first set of samples was based on three different mass ratios of 15/135, 20/130, 25/125, and 30/120 parts paraformaldehyde to UHMW-PE. The second sample set was 5/145 and 10/140 paraformaldehyde to UHMW-PE. Pouches were made using non-woven Tyvek® fabric. A total of 150 mg of each mixture was added to the Tyvek® pouches. The samples made were two repeats for each mixtures pouch type without spore strips and two repeats of each mixtures type with spore strips in the packets.

Details of the formaldehyde testing and response of the spore strips to the prevailing RCS process conditions using the different packages are described in Examples 2 and 3 respectively.

TABLE I

Composition of the Different Packages
Used in the RCS Study of Example I

| Pouch No. | Paraformaldehyde, mg | UHMW-PE, mg |
|---|---|---|
| I-A | 5 | 145 |
| I-B | 10 | 140 |
| I-C | 15 | 135 |
| I-D | 20 | 130 |
| I-E | 25 | 125 |
| I-F | 30 | 120 |

Example 2

Testing for Formaldehyde Residue in Packaged
Sutures of Example 1 due to Pouches I-A to I-F The formaldehyde testing method is described below and the respective results are summarized in Table II. For sample preparation, the packets were tipped with silicone for injecting with a syringe. The sample testing consisted of filling the packets with dry nitrogen. The nitrogen and residual formaldehyde was withdrawn through a 60 mL syringe filled with 1 mL of deionized water. The syringe was then shaken for 15 minutes. The water with dissolved residual formaldehyde was transferred into a 2 mL vial. The samples were tested by complexing with dinitrophenylhydrazine (DNPH) and analyzed using HPLC. The samples were compared to an appropriate formaldehyde standard curve using formaldehyde-DNPH condensation products.

TABLE II

Residual Formaldehyde Tested in Packages
Containing Pouches I-A to I-F

| Packages with Pouch Number. | Residual Formaldehyde in the Package, µg |
|---|---|
| I-A | 26 |
| I-B | 26 |
| I-C | 29 |
| I-D | 29 |
| I-E | 28 |
| I-F | 30 |

The data in Table II show practically the same amounts of formaldehyde regardless of net amount of paraformaldehyde and/or its weight relative to the UHMW-PE dispersant. It appears to be virtually dependent only on the radiation dose.

Example 3

Testing for the Effect of the Process of Spore Strips
in Packages Containing Four Pouches from Example
1 and a Non-Irradiated Control The microbiological methods used in determining the effect of the prevailing RCS process on spore strips is described below and respective results are summarized in Table III.

The spore strip was aseptically placed in 50 mL conical tubes with 9 mL of 0.1% Peptone and vortexed for approximately 5 minutes. The vortexed spore strip suspension was poured through a 40-µm-cell strainer, and then rinsed with an additional 1 ml of Peptone. One milliliter of filtered Peptone solution was pipetted onto Tryptic Soy agar plates and swirled gently to obtain full coverage on plate from eluent. For control (non-sterilized) spore strips, serial dilutions were made to reduce the colony forming units (CFU) to a quantifiable amount after incubation. Of the desired concentration, 1 mL was pipetted onto the agar plate. Plates were incubated at 37° C. and checked periodically for 3 days to monitor growth. All samples were tested in duplicate.

TABLE III

Spore Strip Analysis of Radiochemically Sterilized
Packages Containing Pouches from Example 1

| Packages with Pouch Number | Colony-forming Units |
|---|---|
| I-A | 0 |
| I-B | 0 |
| I-C | 0 |
| I-D | 0 |
| I-E | 0 |
| I-F | 0 |
| Non-irradiated Control (an average of four) | 150* |

*Expected CFUs = 170.

The data in Table III on sterilization effectiveness of the RCS process under the prevailing conditions and package composition show a parallel behavior to that recorded in the results of Table II. Specifically, 5 to 30 mg of paraformaldehyde can release an almost constant amount of formaldehyde, which is quite effective in achieving a complete spore kill.

Example 4

Radiochemical Sterilization of Absorbable
Cyanoacrylate-Based Tissue Adhesive Formulation
Using Different Combinations of Paraformaldehyde
and Silica Gel A typical cyanoacrylate-based tissue adhesive formulation was used which contained about 97, 3, <0.5 and <0.05 weight percent of methoxypropyl cyanoacrylate, a polymeric modifier, free radical stabilizer, and anionic stabilizer, respectively. The polymeric modifier comprised an absorbable, aliphatic, segmented polyether-carbonate-urethane. The formulation was packaged under nitrogen atmosphere in sealed polyethylene dispensers (volume=1 mL) with tapered necks. Each dispenser contained 0.4 mL of liquid formulation. Pairs of the dispensers containing the adhesive formulation were placed in groups of 3"×5" laminated foil packs, each containing a sealed, non-woven polyethylene (Tyvek®) porous pouch filled with different combinations of paraformaldehyde and silica gel as outlined in Table IV. The foil pack containing the tissue adhesive formulation, the porous pouches having the different combinations of paraformaldehyde and silica gel, (average particle size<100 micron) and, in selected cases, a spore strip (for use as a primary control), were purged with nitrogen, heat-sealed, and sterilized under typical RCS conditions as described in Example 1. A number of packages were made without incorporating the pouch for use as secondary controls.

The compositions of the different pouches used in the RCS study of Example 4 are described in Table IV. The preparation of the specific groups of pouches is outlined below. Two sets of packages were prepared. The first and second sets were prepared using 1 to 5 and 1 to 10 weight ratio of paraformaldehyde to silica gel, respectively. The weight of the powder mixture for the first and second set was about 222 and 605 mg, respectively. All packages were purged with nitrogen and sealed. The sealed packages were sterilized by irradiation using about 5 kGy of gamma radiation.

TABLE IV

Composition of Different Packages Used in the RCS Study of Example 4

| Pouch No. | Paraformaldehyde, mg | Silica Gel, mg |
|---|---|---|
| II-A | 37 | 185 |
| II-B | 55 | 550 |

Details of the formaldehyde testing and response of the spore strips to RCS processes using the different package inserts are described in Examples 5 and 6, respectively.

Example 5

Testing for Formaldehyde Residue in Packages II-A and II-B Containing Tissue Adhesives of Example 4

A protocol similar to that described in Example 2 was followed. The respective results are summarized in Table V. The data in Table V indicated no significant dependence of the formaldehyde generation on the amount of paraformaldehyde used.

TABLE V

Residual Formaldehyde Tested in Packages Containing Pouches II-A and II-B

| Packages with Pouch, Number | Residual Formaldehyde at One Week Post-irradiation in Package, μg |
|---|---|
| II-A | 10 |
| II-B | 8 |

Example 6

Testing the Effect of the RCS Process on Packages Containing Two Types of Pouches from Example 4 and a Non-Irradiated Primary and Pouch-Free Secondary Controls A protocol similar to that used in Example 3 was followed. The respective results are summarized in Table VI. The data in Table VI indicate that (1) the two packages sterilized under typical RCS conditions exhibited complete spore kill; (2) the pouch-free packages revealed about 20 percent of spore kill compared to the expected value; and (3) the non-irradiated packages showed practically no effect on the spore strips.

TABLE VI

Spore Strip Analysis of Radiochemically Sterilized Packages Containing Pouches of Example 4 after One Week Post-irradiation and a Pouch-free Control

| Package with and without Pouch Number | Colony-forming Units at Two Weeks Post-irradiation |
|---|---|
| II-A | 0 |
| II-B | 0 |
| II-C[a] | 143 |
| II-D[b] | 166 |

[a]Containing no pouch.
[b]Control (unsterilized) spore strip expected, CFU = 170.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicant hereby discloses all subranges of all ranges disclosed herein. These subranges are also useful in carrying out the present invention.

What is claimed is:

1. A hermetically sealed package for use in radiochemical sterilization of at least one medical device contained therein comprising:
    an essentially gas impervious, moisture impervious sealed outer sheet:
    a holder for the medical device; and
    a sealed, porous pouch contained within the sealed outer sheet and containing a mixture of radiolabile paraformaldehyde particles and radiostable dispersant powder at a weight ratio of less than 1:2.

2. A hermetically sealed package as in claim 1 wherein the outer sheet comprises a laminated foil.

3. A hermetically sealed package as in claim 1 wherein the porous pouch comprises a non-woven fabric construct comprising a polyolefinic material selected from the group consisting of polyethylene, polypropylene, and ethylene-propylene copolymer.

4. A hermetically sealed package as in claim 1 wherein dispersant powder comprises an organic polymer selected from the group consisting of polyethylene, polypropylene, polyethylene terephthalate, and polytetramethylene terephthalate.

5. A hermetically sealed package as in claim 1 wherein the dispersant powder is an inorganic desiccant.

6. A hermetically sealed package as in claim 5 wherein the inorganic desiccant comprises silica gel.

7. A hermetically sealed package as in claim 1 wherein the holder comprises a perforated folder comprising at least one material selected from the group consisting of cellulose, polyethylene, polypropylene, ethylene-propylene copolymer, and polyethylene terephthalate.

8. A hermetically sealed package as in claim 7 wherein the medical device comprises an absorbable suture.

9. A hermetically sealed package as in claim 7 wherein the medical device comprises an absorbable composite surgical mesh.

10. A hermetically sealed package as in claim 7 wherein the medical device comprises a partially absorbable composite surgical mesh.

11. A hermetically sealed package as in claim 7 wherein the medical device comprises a partially absorbable composite vascular repair device.

12. A hermetically sealed package as in claim 7 wherein the medical device comprises a composite urinary bladder repair device.

13. A hermetically sealed package as in claim 7 wherein the medical device comprises a composite polymeric stent for repairing at least one body conduit selected from ureters, urethra, blood vessels, and esophagi.

14. A hermetically sealed package as in claim 7 wherein the medical device comprises an absorbable composite device for internal bone fixation.

15. A hermetically sealed package as in claim 1 wherein the medical device is a cyanoacrylate tissue adhesive and the holder therefor is a gas-tight container.

16. A hermetically sealed package as in claim 15 wherein the gas-tight container is a sealed, squeezable ampoule formed from a polymer selected from the group consisting of polyethylene, polypropylene, ethylene-propylene copolymer, and polyethylene terephthalate.

17. A hermetically sealed package as in claim 15 wherein the gas-tight container is a screw-capped glass vial.

18. A hermetically sealed package as in claim 1 wherein the medical device is a self-setting, composite absorbable bone cement or bone filler and the holder therefor is a squeezable, gas-tight container.

19. A hermetically sealed package as in claim 18 wherein the bone cement or bone filler comprises a cyanoacrylate monomer.

20. A method for radiochemically sterilizing the hermetically sealed package of claim 1 comprising the step of irradiating the package with gamma rays or E-beam at a dose of less than 11 kGy.

* * * * *